(12) United States Patent
Wang

(10) Patent No.: US 10,888,218 B2
(45) Date of Patent: Jan. 12, 2021

(54) VIDEO LARYNGEAL ENDOSCOPE SYSTEM INCLUDING 2D SCAN VIDEO KYMOGRAPHY AND LARYNGEAL STROBOSCOPY

(71) Applicants: UMEDICAL CO., LTD., Busan (KR); Yong Jin Wang, Busan (KR)

(72) Inventor: Yong Jin Wang, Busan (KR)

(73) Assignees: UMEDICAL CO., LTD., Busan (KR); Yong Jin Wang, Busan (KR)

( * ) Notice: Subject to any disclaimer, the term of this patent is extended or adjusted under 35 U.S.C. 154(b) by 382 days.

(21) Appl. No.: 15/557,866

(22) PCT Filed: Nov. 10, 2015

(86) PCT No.: PCT/KR2015/012027
§ 371 (c)(1),
(2) Date: Sep. 13, 2017

(87) PCT Pub. No.: WO2017/022889
PCT Pub. Date: Feb. 9, 2017

(65) Prior Publication Data
US 2018/0049634 A1    Feb. 22, 2018

(30) Foreign Application Priority Data

Aug. 5, 2015  (KR) .................. 10-2015-0110592

(51) Int. Cl.
*A61B 1/267*  (2006.01)
*A61B 1/00*   (2006.01)
(Continued)

(52) U.S. Cl.
CPC .......... *A61B 1/267* (2013.01); *A61B 1/00009* (2013.01); *A61B 1/00045* (2013.01);
(Continued)

(58) Field of Classification Search
CPC . A61B 1/267; A61B 1/00004; A61B 1/00009; A61B 1/00045; A61B 1/00048;
(Continued)

(56) References Cited

U.S. PATENT DOCUMENTS 4,232,685 A * 11/1980 Nagashima ............... A61B 1/04
396/16
7,654,952 B2 * 2/2010 Ott ........................ A61B 1/2673
600/178
(Continued)

FOREIGN PATENT DOCUMENTS

EP      1859727 A1       11/2007
KR  10-1999-0079315 A   11/1999
(Continued)

OTHER PUBLICATIONS

Schutte, Harm K., et al.: First Results of Clinical Application of Videokymography, Laryngoscope, vol. 108 (8, Part 1), pp. 1206-1210, Aug. 1998 (Year: 1998).*
(Continued)

*Primary Examiner* — Ryan N Henderson
(74) *Attorney, Agent, or Firm* — Osha Bergman Watanabe & Burton LLP

(57) ABSTRACT

A video laryngeal endoscope system having flat scan video kymography and laryngoscopic functions for analyzing a motion state of a larynx comprises: a laryngoscope for viewing vocal cords; a light source for illuminating the vocal cords; a video camera which has a beam splitter for separating an image viewed by means of the laryngoscope and the light source into two images to acquire a flat scan kymographic image and a stroboscopic image; a dual image capturing unit for converting two image signals transmitted from the video camera into a digital image signal; a storage unit for storing the digital image signal; a control unit for analyzing the digital image signal of the storage unit and
(Continued)

simultaneously displaying analysis results of the flat scan kymographic image and the stroboscopic image; and a computer comprising analysis software for analyzing the image signal of the storage unit; and a monitor for displaying photographed images and analysis results.

5 Claims, 6 Drawing Sheets

(51) Int. Cl.
*A61B 1/04* (2006.01)
*A61B 1/045* (2006.01)
*A61B 1/06* (2006.01)
*A61B 5/00* (2006.01)

(52) U.S. Cl.
CPC .......... *A61B 1/00193* (2013.01); *A61B 1/042* (2013.01); *A61B 1/045* (2013.01); *A61B 1/0661* (2013.01); *A61B 1/2673* (2013.01); *A61B 1/00006* (2013.01); *A61B 5/0062* (2013.01)

(58) Field of Classification Search
CPC ..... A61B 1/0005; A61B 1/00193; A61B 1/04; A61B 1/042; A61B 1/045; A61B 1/2673; A61B 1/2676; A61B 1/0661; A61B 1/00163; A61B 1/00165; A61B 1/00167; A61B 1/0017; A61B 1/00172; A61B 1/00174; A61B 1/00177; A61B 1/00179; A61B 1/00181; A61B 1/00183; A61B 1/00186; A61B 1/00188; A61B 1/0019; A61B 1/002; A61B 1/05; A61B 1/051; A61B 1/053; A61B 1/055; A61B 17/24
See application file for complete search history.

(56) References Cited

U.S. PATENT DOCUMENTS

| | | | |
|---|---|---|---|
| 9,019,427 B2* | 4/2015 | Laser | A61B 1/00052 348/371 |
| 2003/0139666 A1 | 7/2003 | Klemm et al. | |
| 2005/0219376 A1* | 10/2005 | Wittenberg | A61B 1/042 348/222.1 |
| 2006/0235693 A1* | 10/2006 | Ruderman | A61B 1/2673 704/270 |
| 2007/0208225 A1* | 9/2007 | Czaniera | A61B 1/2673 600/178 |
| 2009/0281390 A1 | 11/2009 | Qiu et al. | |
| 2011/0263935 A1* | 10/2011 | Qiu | G06K 9/6277 600/109 |
| 2014/0161369 A1* | 6/2014 | Ishihara | A61B 1/00009 382/274 |
| 2016/0000370 A1 | 1/2016 | Kim et al. | |

FOREIGN PATENT DOCUMENTS

| | | |
|---|---|---|
| KR | 10 0602498 B1 | 7/2006 |
| KR | 10 2014 0115526 A | 10/2014 |
| KR | 10 2015-0082646 A | 7/2015 |
| WO | 2014/148712 A1 | 9/2014 |

OTHER PUBLICATIONS

Extended European Search Report issued in corresponding European Application No. 15900475.3 dated Mar. 7, 2019 (7 pages).
International Search Report issued in PCT/KR2015/012027 dated May 2, 2016 (6 pages).
Written Opinion of the International Searching Authority issued in PCT/KR2015/012027 dated May 2, 2016 (4 pages).

* cited by examiner (a)  (b)

(a)

(b)

VIDEO LARYNGEAL ENDOSCOPE SYSTEM INCLUDING 2D SCAN VIDEO KYMOGRAPHY AND LARYNGEAL STROBOSCOPY

TECHNICAL FIELD

The present invention relates to a video laryngeal endoscope system having two-dimensional scanning video kymography (2D VKG) and laryngeal stroboscopy functions, and more particularly, to a video laryngeal endoscope system having 2D VKG and laryngeal stroboscopy functions which can simultaneously acquire a 2D VKG image and a laryngeal stroboscopy image by separating an image that can be observed through one laryngoscope into two images.

BACKGROUND ART

The human larynx is a vocal organ for communication by a language, and vocal folds in the larynx vibrate about 100 to 350 times per second according to air flow of an exhale for vocalization. However, in a disease state in which a voice is changed, motions of vocal-fold mucosae become irregular and asymmetric, or vibrations are reduced and may even disappear.

During vocalization, air inhaled into a lower airway increases in pressure due to the vocal folds being closed at a sub-glottis. When the pressure is greater than a resistance of the vocal folds, the vocal folds open, and air flows from the inferior margin of the vocal folds to the superior margin. This air flow leads to mucosal waves in the vocal-fold mucosae, and characteristics, such as a speed, an intensity, and the like, of the mucosal waves determine voice quality. In other words, the vocal folds serve to convert a sub-glottal pressure, which is exerted at the sub-glottis, into acoustic energy while symmetrically and rapidly vibrating at tens to hundreds of hertz. However, a vocal fold nodule, vocal fold paralysis, and the like degrade the symmetry of mucosal waves and preclude an effective energy conversion, thereby leading to trachyphonia (hoarse voice). Therefore, when abnormality of the voice is examined, it is necessary to identify a motion state of the vocal-fold mucosae, that is, vocal-fold vibrations. Among methods currently used for this purpose, there is a method employing a stroboscope. A video stroboscopic method in which a stroboscope is used to observe vocal folds' rapid motions of 100 to 350 times per second at slow motion is primarily used. However, there is a fundamental problem in that images which can be observed through videostroboscopy do not actually show vibrations of vocal folds corresponding to one accurate cycle (period). Also, meaningful interpretation is not possible when there is a wide variation in vocal-fold motion between cycles or when there is a large gap between vocal folds during vocalization and periodic repetitiveness is absent, that is, in the case of a patient with aperiodic dysphonia. Therefore, there is no choice but to qualitatively describe overall motions of the vocal-fold mucosae. Further, it is necessary to solve a problem in that it is not possible to separately identify a minute motion of a part, all, or a particular part of vocal-fold mucosae and the like. Moreover, since stroboscopic images are subjectively observed, a determination of a skilled expert is required for accurate interpretation.

Here, a stroboscope necessarily requires a light source, and a strobe light source emits light intermittently and not continuously toward an object which moves at high speed. A charge-coupled device (CCD) camera acquires an image only while the light source is turned on and shows the acquired image on a monitor. By adjusting a rate at which the strobe light source is turned on and off, it is possible to obtain images of an object which moves at low speed. However, a conventional stroboscope has problems in that a light source device for producing a strobe light source which intermittently emits light is configured to have a large volume and a heavy weight, consumes much power, and has a high equipment price. Also, the conventional stroboscope has a problem in that when the strobe light source is not synchronized with a sampling rate of a camera, images are darkened and a target object may not be clearly observed.

As another vocal-fold vibration examination method for overcoming these disadvantages, line scanning video kymography (VKG) technique has been developed by Svec et al. (Svec JG and Schutte HK) in 1996. This is a method of acquiring images of a continuous motion at approximately 8000 frames per second on a part, that is, one line, of a vocal fold arbitrarily selected by an examiner during an examination and displaying the acquired images on a monitor. In other words, as shown in FIG. 1, a part of vocal folds having a slit is photographed at a high rate so that a motion of only the part is photographed. However, this method has a disadvantage in that it is not observation of the entirety of the vocal folds but evaluation of a part of one line. In other words, when an examinee makes a vocalization once, only a kymogram for one line can be acquired, and since a motion of an entire region cannot be observed while the kymogram is acquired, there are problems in that there is no criterion to properly determine distortion caused by a motion of a patient and the like.

In addition, a method using multi-line VKG by readjusting images taken by ultra-high speed digital imaging also exists. However, this method is the same as line scanning VKG in that the entirety of the vocal folds is not observed, and has many limitations in use because subsidiary equipment, such as an expensive CCD camera which is particularly devised and the like, is required.

To solve the problems of line scanning VKG and ultra-high speed digital imaging, two-dimensional scanning VKG (2D VKG) for examining a vibration state of an entire vocal-fold region in real time by using the principle of laryngeal photokymography has been developed. 2D VKG makes it possible to avoid distortion caused by a motion of a patient and the like, extract subjective indices from stored images by using computer software, quantify the subjective indices with minimum intervention of a user, and also analyze mucosal motion states by comparing and observing an entire region of both vocal folds. However, according to 2D VKG, since vocal folds are shown in the form of a diamond in a distorted manner to express motions of the entirety of the vocal folds, it is not possible to show actual motions of the vocal folds, unlike laryngeal stroboscopy.

DISCLOSURE

Technical Problem

The present invention is directed to providing a video laryngeal endoscope system which simultaneously provides a two-dimensional scanning video kymography (2D VKG) function and a laryngeal stroboscopy function and in which a rigid or curved laryngoscope uses a continuous light source rather than an intermittent light source, a beam splitter is used to separate an image that can be observed through one laryngoscope into two images, and the separated images are separately projected by two camera modules so that vocal folds can be simultaneously photographed in two ways.

The present invention is also directed to providing a video laryngeal endoscope system which has a 2D VKG function for extracting a vibration state of an entirety of vocal-fold regions rather than a part of the vocal folds in real time and analyzing mucosal motion states of the entirety of the vocal-fold regions, and also a function for acquiring laryngeal stroboscopy images by using a continuous light source passed through a beam splitter rather than a strobe light source intermittently emitting light.

Technical Solution

One aspect of the present invention provides a video laryngeal endoscope system having two-dimensional scanning video kymography (2D VKG) and laryngeal stroboscopy functions, the system including: a laryngoscope configured to observe vocal folds; a light source configured to illuminate the vocal folds; a video camera configured to have a beam splitter for separating the light source into two light sources and acquire a 2D VKG image and a stroboscopic image; a computer including a dual image capturing unit configured to convert two video signals transmitted from the video camera into digital image signals, a storage unit configured to store the digital image signals, a control unit configured to cause the image signals of the storage unit to be analyzed and simultaneously display analysis results of the 2D VKG images and the stroboscopic images on a monitor, and analysis software configured to analyze the image signals of the storage unit; and the monitor configured to simultaneously display the 2D VKG images and the stroboscopic images and display the analysis results.

Preferably, the video camera may include a first camera module configured to have a rolling shutter and acquire 2D VKG image by scanning vocal-fold mucosae, and a second camera module configured to acquire the stroboscopic images.

Preferably, the first camera module and the second camera module may have a shutter speed of $1/1000$ second or faster.

Preferably, the second camera module may acquire an optical signal provided by light obtained from the light source as an analog image signal, convert the analog image signal into a digital image signal, and adjust a shutter time and a sampling rate.

Preferably, the light source may be a continuous xenon light source.

Another aspect of the present invention provides a method of analyzing a laryngeal motion state performed in a video laryngeal endoscope system having 2D VKG and laryngeal stroboscopy functions, the method including: (a) storing kymograph images obtained by photographing motions of vocal folds by using a laryngoscope, a light source, and a video camera and stroboscopic images obtained by photographing a motion of a glottis in a storage unit through a dual image capturing unit; (b) forming, by a control unit, a predetermined number of image frames of the storage unit by frames, displaying the image frames on a monitor, configuring and displaying a menu screen so that a user can select a frame that he or she wants to observe with a mouse or a keyboard; and (c) analyzing, by analysis software, the kymograph images and the stroboscopic images and simultaneously displaying normalized indices of the observed vocal folds and glottis.

Preferably, step (a) may include photographing entirety of the vocal folds and the glottis without vocalization and then photographing motions of entirety of vibration parts of the vocal folds and a motion state of the glottis during vocalization of "i" or "eh."

Preferably, the normalized indices of step (c) may include an average vocal-fold width with respect to a longitudinal-axial length of the glottis, a glottis opening ratio, which is a ratio of a vocal-fold opening period to a total period, an asymmetry index, which is a difference in degree of opening between the both vocal folds, a basic frequency, a vibration strength, regularity of vibration, a mucosal wave, symmetricity of the vibration, an outer boundary shape, an inner boundary shape, an abnormal cycle, or vibration absence of vocal-fold mucosae.

Advantageous Effects

As described above, according to the present invention, since it is possible to compare two-dimensional scanning video kymography (2D VKG) images and stroboscopic images of an entire region of vocal folds in real time, diagnosis of a laryngeal motion and subsequent prognosis tracking are easy.

Also, the 2D VKG images and the stroboscopic images are stored such that an examiner can carefully and repeatedly observe the images through a video to objectively analyze indices including a basic frequency, a mucosal wave, symmetricity of vibration, a vibration strength, regularity of the vibration, a phase difference, absence of vibration of the vocal-fold mucosae, interference of surroundings with the vocal folds, duration of glottal closure, left-right asymmetry, presence of mucosal waves, type of cycle-to-cycle variability, shapes of the lateral and medial peaks, cycle aberrations, and the like, which are more accurate and meaningful parameters, and preserve an examination result. Further, since the normalized indices according to the present invention are useful in visualizing and quantifying a vibration state of the vocal folds, it is possible to objectively evaluate a laryngeal function.

Moreover, the present invention has a simple configuration, a small volume, and a lightweight when compared to a conventional stroboscope, and thus is economically advantageous. Also, since a 2D VKG image and a stroboscopic image can be acquired by one photography operation and observed, it is possible to accurately analyze the aforementioned parameters. Therefore, the present invention can be used by many people in a wide variety of medical or industrial fields.

MODES OF THE INVENTION

Hereinafter, exemplary embodiments of the present invention will be described in detail with reference to the accompanying drawings. However, the following exemplary embodiments are provided for those of ordinary skill in the art to sufficiently appreciate the present invention, and various modifications can be made thereto. The scope of the present invention is not limited to the exemplary embodiments described below.

Figure 1:
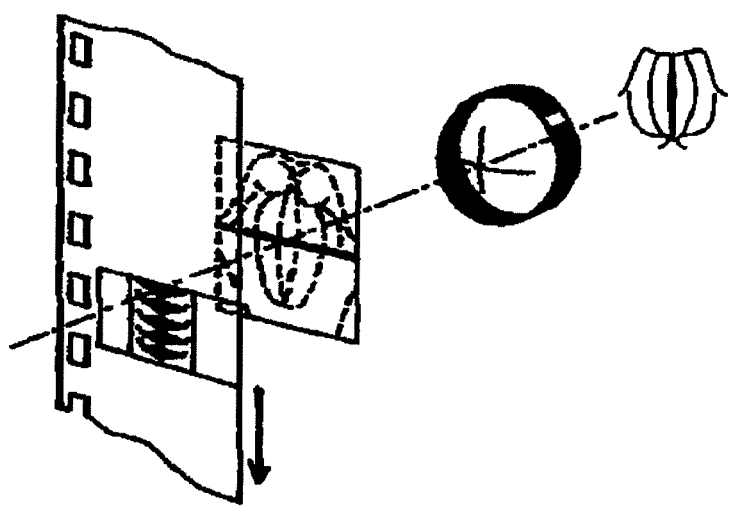
FIG. 1 is a schematic diagram illustrating a principle of line scanning video kymography (VKG) according to a conventional art.
Figure 2:
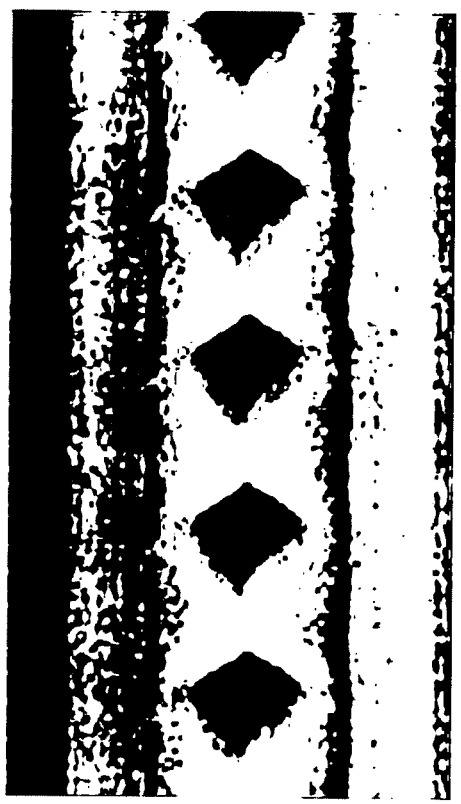
FIG. 2 is an image screen photographed by a line scanning VKG system according to a conventional art.
Figure 3:
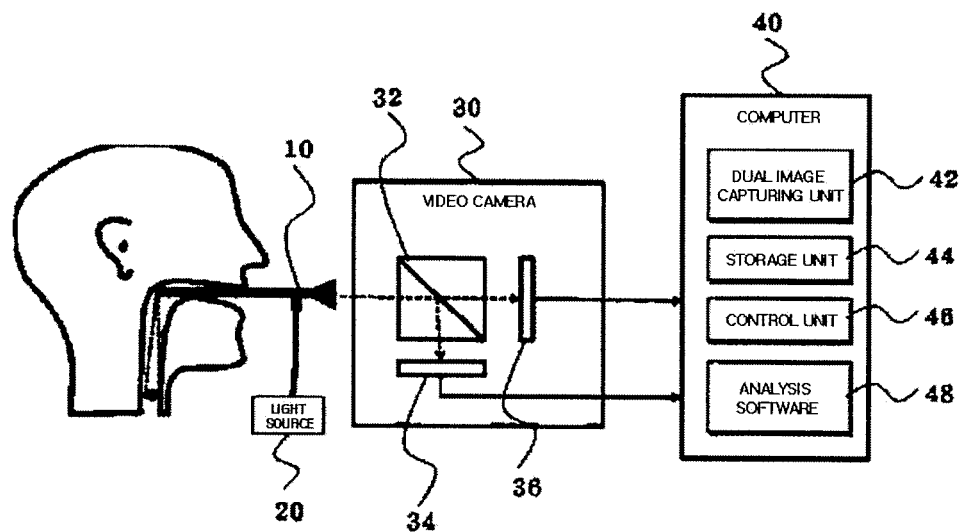
FIG. 3 is a schematic block diagram of a video laryngeal endoscope system having two-dimensional scanning VKG (2D VKG) and laryngeal stroboscopy functions according to an exemplary embodiment of the present invention.

FIG. 3 is a schematic block diagram of a video laryngeal endoscope system having two-dimensional scanning video kymography (2D VKG) and laryngeal stroboscopy functions according to an exemplary embodiment of the present invention. A video laryngeal endoscope system having the 2D VKG and laryngeal stroboscopy functions for analyzing a laryngeal motion state according to an exemplary embodiment of the present invention includes a laryngoscope 10, a light source 20, a video camera 30, a computer 40, and a monitor (not shown). Here, the video camera 30 includes a beam splitter 32, a first camera module 34, and a second camera module 36, and the computer 40 includes a dual image capturing unit 42, a storage unit 44, a control unit 46, and analysis software 48.

In a configuration of FIG. 3, the laryngoscope 10, which is a tool for observing vocal folds, is connected to the video camera 30 and makes it possible to take an image of a larynx including vocal folds and a glottis. Both a rigid type of laryngoscope and a curved type of laryngoscope may be used as the laryngoscope 10.

In an exemplary embodiment, the laryngoscope 10 may be integrally implemented with the video camera 30, which will be described below.

The video camera 30 is a device for recording and storing images observed through the laryngoscope 10. More specifically, the video camera 30 has the beam splitter 32 to separate an image taken by the laryngoscope 10 into two images and extracts 2D VKG and stroboscopy images by causing the first camera module 34 and the second camera module 36 to project two separated images.

The first camera module 34 extracts 2D VKG image rather than line scanning kymography image based on a conventional art. The first camera module 34 will be described in detail below with reference to FIGS. 4 and 5.

The second camera module 36 acquires a stroboscopic image by processing and observing an image of the glottis of the larynx which makes periodic motions at a high rate. More specifically, the second camera module 36 acquires an optical signal provided by images obtained by the laryngoscope 10 and the light source 20 as an analog image signal, converts the analog image signal into a digital image signal, and adjusts a shutter time and a sampling rate. In other words, the second camera module 36 samples a periodic motion of a target object, which is repeated at a high rate, at an appropriately low rate so that one-period elements of the repeated motions can be completely extracted.

For example, the second camera module 36 may be implemented as a charge-coupled device (CCD) camera, and a function of the second camera module 36 may be implemented through a digital signal process (DSP) in a full high-definition (HD) camera.

In an exemplary embodiment, the second camera module 36 images a glottal motion according to the adjusted shutter time and sampling rate. More specifically, the second camera module 36 preferably has a short shutter time. When the shutter time is long, one image is acquired as continuous images rather than a still image and an observer cannot clearly observe a state in which a target object makes periodic motions.

In an exemplary embodiment, the second camera module 36 may adjust the shutter time according to brightness of the light source 20 and adjust the sampling rate to show a high-speed motion of a laryngeal glottis which cannot be observed with the naked eye as images of a low-speed motion or a still image. In other words, it is possible to observe whether the larynx is accurately closed and opened. For example, when the glottis of the larynx is opened and closed 100 to 250 times per second for vocalization, the shutter time of the second camera module 36 may be adjusted to have a time interval corresponding to 0.35 periods or less (preferably 0.1 periods or less) as a result of analyzing the glottal motion of the larynx, and the sampling rate may be adjusted so that a glottal motion output to a monitor can be accurately observed. A process in which sequential still images are continuously output through the monitor may be repeated to show the imaged glottal motion.

The second camera module 36 may clearly observe a target object by using the continuous light source 20 rather than an intermittent light source according to a conventional stroboscopic method and thus extracts a stroboscopic image which is superior in terms of performance.

The computer 40, which is a general-use personal computer, includes the image capturing unit 42, the storage unit 44, the control unit 46, and the analysis software 48. The dual image capturing unit 42, which is in the form of an image capture board, serves to convert a video signal transmitted from the video camera 30 into a digital image signal which can be processed by the computer 40, and may employ a general-use image signal processing board which facilitates editing of various images. Generally, an auxiliary substrate type, which may be inserted into a mainboard extension bus of the computer 40 in a slot form, may be used.

The control unit 46 of the computer 40 stores a digital image signal of, for example, 25 to 30 consecutive frames per second transmitted from the dual image capturing unit 42 in the storage unit 44 and then controls the analysis software 48 to analyze a laryngeal motion state. In other words, the control unit 46 analyzes the image signal moved to the storage unit 44 to visualize analysis results of 2D VKG images and stroboscopic images, that is, a vibration state of the vocal folds and a motion state of the glottis, on the monitor (not shown), and displays a quantified clinical index.

Figure 4:
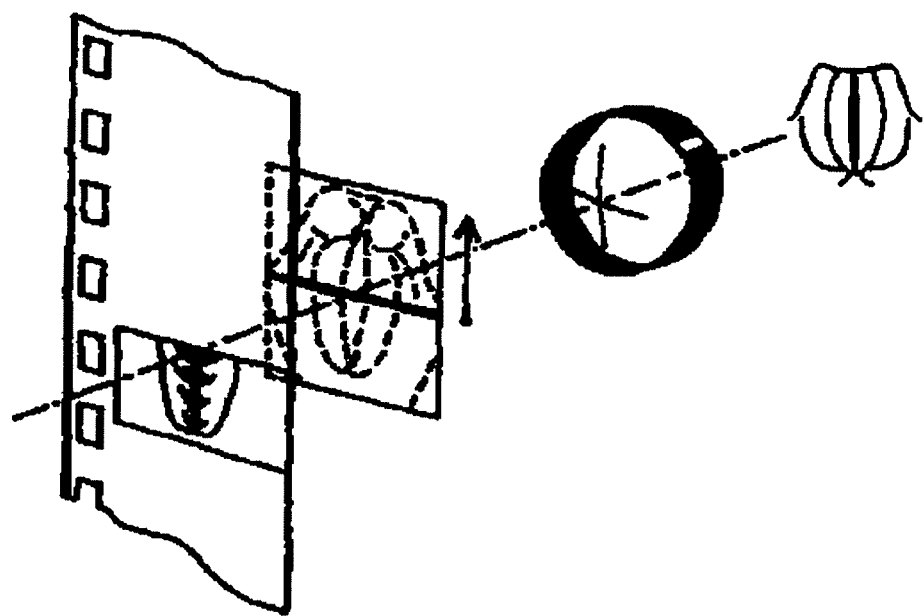
FIGS. 4 and 5 are schematic diagrams illustrating a principle of 2D VKG used in the present invention, FIG. 4 showing a principle of scanning an entirety of vocal folds, that is, 2D scanning, and FIG. 5 showing images of the entirety of the vocal folds obtained by 2D scanning.
Figure 5:
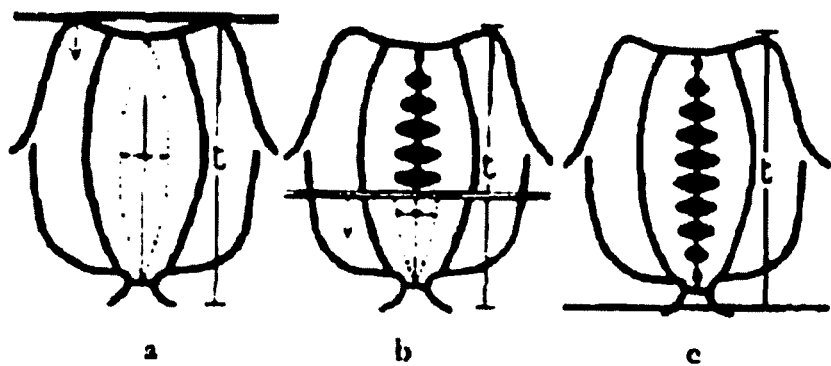

FIGS. 4 and 5 are diagrams illustrating a principle of 2D VKG used in the present invention. As shown in FIG. 4, for 2D VKG, the first camera module 34 of the video camera 30 is placed in a still state, and vocal-fold mucosae are scanned through a gap of a moving slit so that the entirety of the vocal folds are scanned, that is, 2D scanning is performed.

Specifically, as shown in FIG. 5, a thin slit shutter moves on a plane of vocal-fold images and film is exposed during the movement. Since images acquired through such a procedure sequentially show several image rows obtained by capturing an entire image of the larynx in different temporal steps as one entire image, dynamic images of the entire larynx are shown.

To this end, the first camera module 34 of the video camera 30 operates in a highly sensitive high-resolution manner and has a rolling shutter. Preferably, the first camera module 34 may use a rolling shutter type complementary metal oxide semiconductor (CMOS) camera module, and a shutter speed may be set to a high speed of 1/1000 second or faster to increase a resolution of images. In this case, a screen may be very dark, and thus a high-sensitivity and high-luminance light source may be used as the light source 20. Preferably, a very bright xenon light source is used as the light source 20 which illuminates the vocal folds. In the present invention, the very bright continuous light source may be used as the light source 20 instead of an intermittent light source (a strobe light source) used in the conventional stroboscopic method.

While normal people or patients having an abnormal vocal-fold function are caused to vocalize a specific sound ("i" or "eh") in a comfortable state, the vocal folds are photographed using the laryngoscope 10, the light source 20, and a rolling shutter camera corresponding to the first camera module 34. In this way, videos having a predetermined number, for example, 25 to 30, of consecutive frames per second are recorded as images recorded in a predetermined format, for example, an AVI format, and the recorded videos are played and output.

Next, a method of analyzing a laryngeal motion state according to an exemplary embodiment of the present invention in the above-described video laryngeal endoscope system having the 2D VKG and laryngeal stroboscopy functions will be described in detail with reference to the accompanying drawings.

Figure 6:
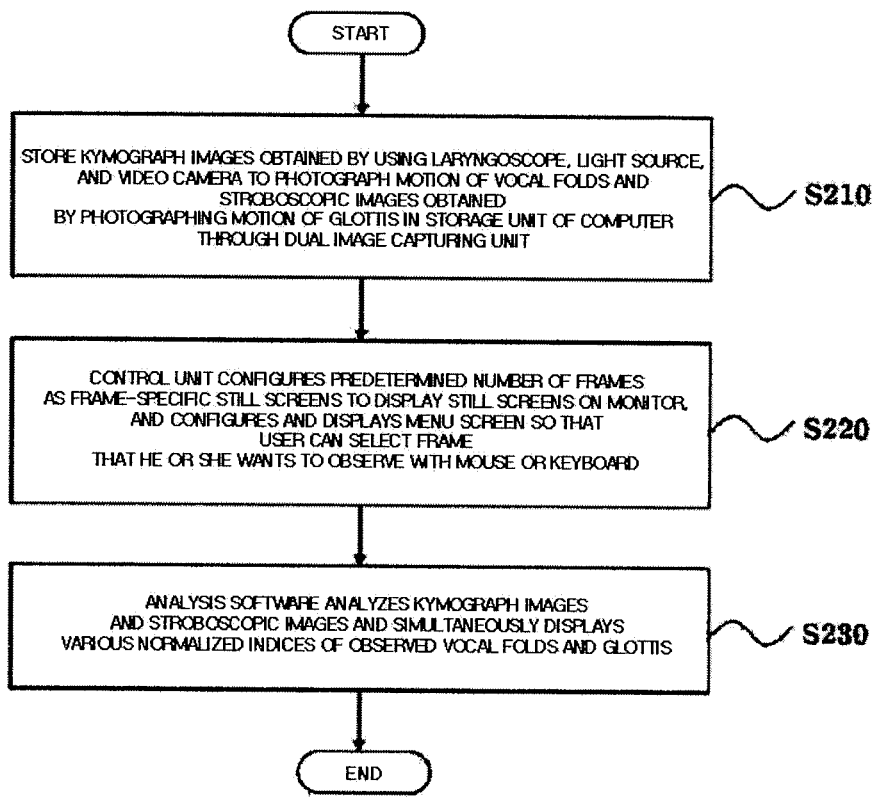
FIG. 6 is a flowchart illustrating a method of analyzing a laryngeal motion state by a video laryngeal endoscope system having 2D VKG and laryngeal stroboscopy functions according to an exemplary embodiment of the present invention.

FIG. 6 is a flowchart illustrating a method of analyzing a laryngeal motion state by the video laryngeal endoscope system having the 2D VKG and laryngeal stroboscopy functions according to an exemplary embodiment of the present invention. Referring to FIG. 6, first, kymograph images obtained by photographing motions of vocal folds using the laryngoscope 10, the light source 20, and the video camera 30 and stroboscopic images obtained by photographing a motion of a glottis are stored in the storage unit 44 of the computer 40 through the dual image capturing unit 42 (step S210).

To analyze a laryngeal motion state, for example, the entirety of the vocal folds are photographed without vocalization. Then, during vocalization of "i" or "eh," motions of the entirety of vocal-fold vibration parts are photographed and converted into 2D scanning kymograms and a motion state of the glottis is observed to acquire stroboscopic images.

Next, the control unit 46 of the computer 40 forms a predetermined number of frames as frame-specific still screens to display the still screens on the monitor, and configures and displays a menu screen so that a user can select a frame that he or she wants to observe with a mouse or a keyboard (step S220).

Next, the analysis software 48 of the computer 40 analyzes the kymograph images and the stroboscopic images and normalizes and displays various indices of the vocal folds and the glottis, for example, an average vocal-fold width with respect to a longitudinal-axial length of the glottis, a glottis opening ratio, which is a ratio of a vocal-fold opening period to a total period, an asymmetry index, which is a difference in degree of opening between the both vocal folds, a basic frequency, a vibration strength, regularity of vibration, a mucosal wave, symmetricity of the vibration, an outer boundary shape, an inner boundary shape, an abnormal cycle, vibration absence of vocal-fold mucosae, and the like (step S230). Using these indices, it is possible to evaluate a state more objectively and accurately.

A 2D VKG image acquired by the video laryngeal endoscope system having the 2D VKG and laryngeal stroboscopy functions according to the present invention will be described below with reference to FIGS. 7 to 11 in comparison with the conventional art.

Figure 7:
FIG. 7 is a laryngeal endoscope image screen of a normal person.
Figure 8:
FIGS. 8 to 10 are 2D VKG image screens acquired according to the present invention.
Figure 9:
Figure 10:

FIG. 7 is a laryngoscope image screen of a normal person, and FIGS. 8 to 10 show 2D VKG image screens photographed by the video laryngeal endoscope system having the 2D VKG and laryngeal stroboscopy functions according to the present invention. FIGS. 8 to 10 are 2D VKG image screens of a normal adult male during vocalization, and 25 to 30 consecutive frames of video images stored in a digital format are moved to the storage unit 44 of the computer 40 by using the dual image capturing unit 42 and then displayed on the monitor (not shown).

Specifically, FIG. 8 is a 2D VKG image screen of a normal man during low-voice vocalization, FIG. 9 is a 2D VKG image screen of a normal man during high-voice vocalization, and FIG. 10 is a 2D VKG image screen of a normal man during falsetto-voice vocalization.

Figure 11:
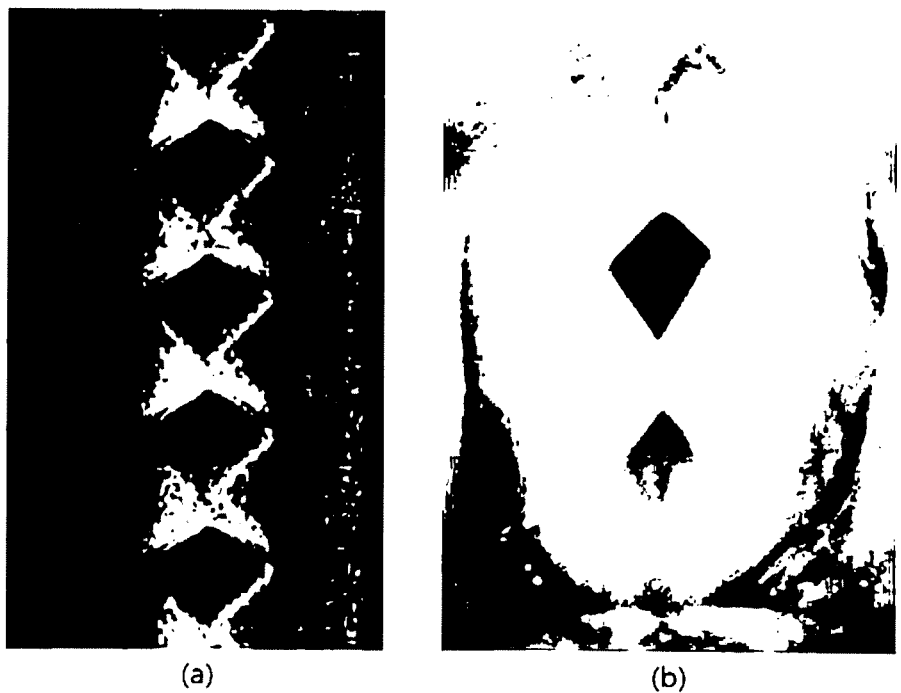
FIG. 11 shows comparative images of line scanning kymography according to a conventional art and 2D VKG according to the present invention.

FIG. 11 shows comparative images of line scanning VKG (a) according to the conventional art and 2D VKG (b) according to the present invention.

(a) of FIG. 11 is line scanning kymography for photographing a motion of a part of vocal folds. (a), which is an image according to the conventional art, has a disadvantage in that it is not an observation of the entirety of the vocal folds but an evaluation of a part of one line. In other words, when an examinee makes a vocalization once, only a kymogram for one line can be acquired, and since a motion of an entire region cannot be observed while the kymogram is acquired, there are problems in that there is no criterion to properly determine distortion caused by a motion of a patient and the like. (b) of FIG. 11 is a 2D VKG image obtained by photographing motions of the entirety of the vocal folds according to the present invention. According to the image of (b), motions of the entirety of the vocal folds may be observed in real time by overcoming the disadvantages of the image of (a), and thus it is possible to minimize distortion caused by a motion of the patient and the like.

Figure 12:
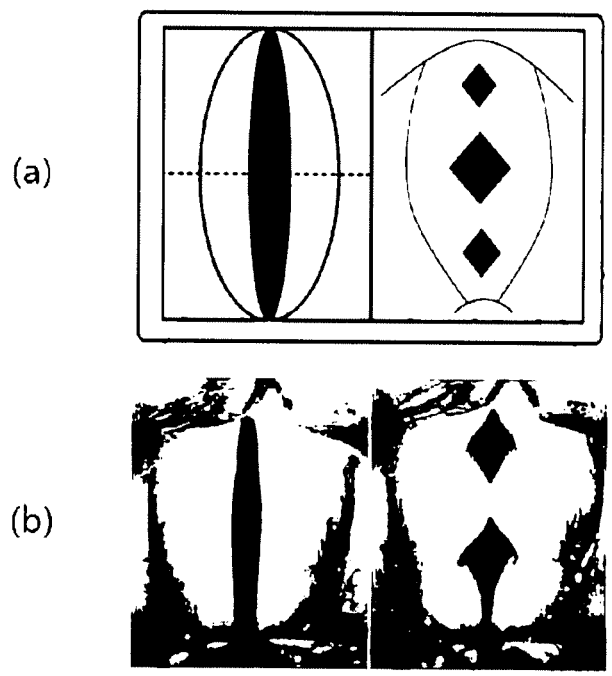
FIG. 12 shows image screens photographed by a video laryngeal endoscope system having 2D VKG and laryngeal stroboscopy functions according to the present invention.

FIG. 12 shows image screens photographed by a video laryngeal endoscope system having the 2D VKG and laryngeal stroboscopy functions according to the present invention.

Referring to FIG. 12, it is possible to simultaneously acquire a 2D VKG image and a stroboscopic image by using the video laryngeal endoscope system having the 2D VKG and laryngeal stroboscopy functions according to the present invention.

Referring to (a) of FIG. 12, a concept of an image which may be acquired through the present invention is shown. The video laryngeal endoscope system having the 2D VKG and laryngeal stroboscopy functions according to the present invention is used to simultaneously acquire a 2D VKG image and a stroboscopic image, and the stroboscopic image and the 2D VKG image are respectively disposed on the left and right sides to be displayed as shown in (a) of FIG. 12 so that an observer can simultaneously view the two images. In an exemplary embodiment, the disposition of the 2D VKG image and the stroboscopic image may be changed by a setting of the observer.

Referring to (b) of FIG. 12, as an example of images which may be acquired through the present invention, an image on the left side is a stroboscopic image and an image on the right side is a 2D VKG image. Since the two images can be simultaneously acquired and simultaneously displayed due to the present invention, a state of a larynx can be determined more objectively and accurately.

In other words, conventionally, it is possible to take and acquire only a stroboscopic image or a 2D VKG image, whereas the present invention can use the light source 20 and the video camera 30 including the beam splitter 32, the first camera module 34, and the second camera module 36 to simultaneously acquire and display a stroboscopic image and a 2D VKG image.

Although exemplary embodiments of a video laryngeal endoscope system having the 2D VKG and laryngeal stroboscopy functions according to the present invention have been described above, the present invention is not limited thereto. Rather, the present invention can be varied in various ways within the scope of the claims, the detailed description thereof, and the appended drawings, and the variations still fall within the present invention.

The invention claimed is:

1. A video laryngeal endoscope system having two-dimensional scanning video kymography (2D VKG) and laryngeal stroboscopy functions; the system comprising:

a laryngoscope configured to observe vocal folds;

a light source configured to illuminate the vocal folds;

a video camera configured to have a beam splitter for separating an image observed through the laryngoscope and the light source to acquire a 2D VKG image and a stroboscopic image;

a computer configured to convert signals including 20 VKG images and stroboscopic images transmitted from the video camera into digital image signals, store the digital image signals, analyze the stored digital image signals and simultaneously display analysis results of the 2D VKG image and the stroboscopic image on a monitor; and the monitor configured to simultaneously display the 2D VKG image and the stroboscopic image and display the analysis results comprising normalized indices of the observed vocal folds and glottis, wherein the normalized indices comprise a glottis opening ratio.

2. The video laryngeal endoscope system of claim 1, wherein the video camera comprises:

a first camera module configured to have a rolling shutter and acquire 2D VKG image by scanning vocal-fold mucosae; and a second camera module configured to acquire the stroboscopic image.

3. The video laryngeal endoscope system of claim 2, wherein the first camera module and the second camera module have a shutter speed of $1/1000$ second or faster.

4. The video laryngeal endo scope system of claim 2, wherein the second camera module acquires an optical signal provided by the image obtained by the laryngoscope and the light source as an analog image signal, converts the analog image signal into a digital image signal, and adjusts a shutter time and a sampling rate.

5. The video laryngeal endoscope system of claim 1, wherein the light source is a continuous xenon light source.

* * * * *